United States Patent
Hill, III et al.

(10) Patent No.: US 6,746,446 B1
(45) Date of Patent: *Jun. 8, 2004

(54) ELECTROPHYSIOLOGICAL DEVICE FOR THE ISTHMUS

(75) Inventors: E. Richard Hill, III, Berkeley, CA (US); Sung Chun, Palo Alto, CA (US); Reynaldo P. Hilario, Mountain View, CA (US); Tim Ngeo Huynh, Santa Clara, CA (US); Mahmoud R. Seraj, Mountain View, CA (US); Robert Obara, Fremont, CA (US)

(73) Assignee: Cardima, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 58 days.

(21) Appl. No.: 09/633,054

(22) Filed: Aug. 4, 2000

(51) Int. Cl.$^7$ ............................................. A61B 18/18
(52) U.S. Cl. ........................................ 606/41; 604/95.04
(58) Field of Search ..................... 606/38–42, 45–50; 600/372, 374, 381, 383; 607/100–102, 122, 99, 113; 604/95.04

(56) References Cited

U.S. PATENT DOCUMENTS

| | | |
|---|---|---|
| 4,488,561 A | 12/1984 | Doring |
| 4,633,880 A | 1/1987 | Osypka et al. |
| 4,665,906 A | 5/1987 | Jervis |
| 4,777,955 A | 10/1988 | Brayton et al. |
| 5,056,526 A | 10/1991 | Khalil |
| 5,067,957 A | 11/1991 | Jervis |
| 5,170,787 A | 12/1992 | Lindegren |
| 5,190,546 A | 3/1993 | Jervis |
| 5,217,027 A | 6/1993 | Hermens |
| 5,228,442 A | 7/1993 | Imran |
| 5,231,989 A | 8/1993 | Middleman et al. |
| 5,242,441 A | 9/1993 | Avitall |

(List continued on next page.)

FOREIGN PATENT DOCUMENTS

WO     WO 95/13111     5/1995

*Primary Examiner*—Michael Peffley
*Assistant Examiner*—Peter J Vrettakos
(74) *Attorney, Agent, or Firm*—Fitch, Even, Tabin & Flannery (57) ABSTRACT

An intravascular electrophysiology (EP) device for the mapping and/or formation of lesions along the isthmus region of a heart that has particular utility in the treatment of atrial flutter. The EP device of the invention has an elongated shaft with a proximal section, a compound-curved or modified pigtail-shaped distal section, and a plurality of at least partially exposed electrodes disposed on an outer surface of the distal section. The electrodes are spaced along a length of the distal section and may be interspersed with at least one temperature sensor located between electrodes. The shape of the distal end of the device enables manipulation of the device by inserting its distal end in the tricuspid valve and retracting the device to bias the section having electrodes along the isthmus to achieve acceptable contact with the region so high frequency (e.g., RF) electrical energy delivered to the electrodes on the distal section of the EP device will form a lesion. Sections of the isthmus where treatment is desired but not reached by the section of the device biased against tissue by retraction may be ablated by repeating the steps of hooking the tricuspid valve at a different end location of the device and retracting to bias the electrodes against different tissue, simply advancing the section with electrodes to the desired site or retracting the device so a tip connected to an RF source will drop into a desired site where ablation may occur.

8 Claims, 6 Drawing Sheets

U.S. PATENT DOCUMENTS

| | | | |
|---|---|---|---|
| 5,290,229 A | * | 3/1994 | Paskar .................... 604/95.04 |
| 5,304,131 A | * | 4/1994 | Paskar .................... 604/95.04 |
| 5,350,419 A | | 9/1994 | Bendel et al. |
| 5,354,297 A | | 10/1994 | Avitall |
| 5,387,233 A | | 2/1995 | Alferness et al. |
| 5,431,683 A | | 7/1995 | Bowald et al. |
| 5,441,483 A | * | 8/1995 | Avitall .................... 604/95 |
| 5,462,545 A | | 10/1995 | Wang et al. |
| 5,465,717 A | | 11/1995 | Imran et al. |
| 5,478,330 A | | 12/1995 | Imran et al. |
| 5,482,037 A | | 1/1996 | Borghi |
| 5,509,411 A | | 4/1996 | Littmann et al. |
| 5,531,781 A | * | 7/1996 | Alferness et al. ........... 607/122 |
| 5,582,609 A | | 12/1996 | Swanson et al. |
| 5,673,695 A | | 10/1997 | McGee et al. |
| 5,722,400 A | | 3/1998 | Ockuly et al. |
| 5,769,847 A | * | 6/1998 | Panescu et al. .............. 606/42 |
| 5,782,760 A | | 7/1998 | Schaer |
| 5,823,955 A | | 10/1998 | Kuck et al. |
| 5,860,920 A | | 1/1999 | McGee et al. |
| 5,863,291 A | | 1/1999 | Schaer |
| 5,865,800 A | | 2/1999 | Mirarchi et al. |
| 5,871,444 A | | 2/1999 | Ouchi |
| 5,871,523 A | | 2/1999 | Fleischman et al. |
| 5,876,373 A | | 3/1999 | Giba et al. |
| 5,876,385 A | | 3/1999 | Ikari et al. |
| 5,879,295 A | | 3/1999 | Li et al. |
| 5,879,296 A | | 3/1999 | Ockuly et al. |
| 5,882,333 A | | 3/1999 | Schaer et al. |
| 5,885,259 A | | 3/1999 | Berg |
| 5,885,272 A | | 3/1999 | Aita et al. |
| 5,885,278 A | * | 3/1999 | Fleischman .................. 606/41 |
| 5,891,109 A | | 4/1999 | Inoue et al. |
| 5,895,355 A | | 4/1999 | Schaer |
| 5,895,417 A | | 4/1999 | Pomeranz et al. |
| 5,897,529 A | | 4/1999 | Ponzi |
| 5,902,291 A | | 5/1999 | Houser et al. |
| 5,906,590 A | | 5/1999 | Hunjan et al. |
| 5,906,613 A | | 5/1999 | Mulier et al. |
| 5,908,446 A | | 6/1999 | Imran et al. |
| 5,913,854 A | | 6/1999 | Maguire et al. |
| 5,916,209 A | | 6/1999 | Mick |
| 5,916,213 A | | 6/1999 | Haissaguerre et al. |
| 5,916,214 A | | 6/1999 | Cosio et al. |
| 5,921,924 A | | 7/1999 | Avitall |
| 5,928,276 A | | 7/1999 | Griffin, III et al. |
| 5,931,811 A | | 8/1999 | Haissaguerre et al. |
| 6,129,724 A | * | 10/2000 | Fleischman et al. .......... 606/41 |
| 6,251,107 B1 | * | 6/2001 | Schaer ....................... 606/41 |
| 6,458,107 B1 | * | 10/2002 | Ockuly ....................... 600/381 |

* cited by examiner

ELECTROPHYSIOLOGICAL DEVICE FOR THE ISTHMUS

FIELD OF THE INVENTION

This relates to the elimination of cardiac arrhythmia, particularly, atrial flutter by interrupting signals crossing the so-called isthmus region of the heart through electrophysiological (EP) treatment.

BACKGROUND OF THE INVENTION

Cardiac arrhythmia presently affects approximately 2 million people in the United States alone. A first type of arrhythmia, atrial fibrillation, is the disorganized depolarization of a patient's atrium, with little or no effective atrial contraction. Various uncoordinated stages of depolarization and repolarization, due to multiple reentry circuits within the atria, cause, instead of intermittent contraction, quivering in a chaotic pattern that results in an irregular and often rapid ventricular rate. A second type, atrial flutter, is a condition in which atrial contractions are rapid (250 to 300 beats per minute), but regular. In many instances, a circus movement caused by reentry is probably present. The condition is such that the ventricles are unable to respond to each atrial impulse so that at least a partial atrioventricular block develops. Either condition may be chronic or intermittent. It is atrial flutter that the present invention is most intended to address.

Prior methods for treating a patient's arrhythmia include the use of antiarrhythmic drugs such as sodium and calcium channel blockers or drugs which reduce the Beta-adrenergic activity. Other methods include surgically sectioning the origin of the signals causing the arrhythmia, or the conducting pathway for such signals. However, the surgical technique is quite traumatic and is unacceptable to a large number of patients. A more frequently used technique to terminate the arrhythmia involves destroying the heart tissue which causes the arrhythmia by heat, e.g., applying a laser beam or high frequency electrical energy, such as RF or microwave, to a desired arrhythmogenic site on the patient's endocardium. In the latter method, intravascular (EP) devices can be used to form contiguous lesions within a patient's atrial chamber to provide results similar to the surgical segregation techniques in terminating the arrhythmia but with significantly reduced trauma.

Typically, an EP device is advanced within a patient's vasculature and into a heart chamber and a lesion is formed at the site of interest when RF electrical energy is emitted from electrodes of the device. RF ablation techniques produce lesions of a generally small area. Consequently, several lesions are typically needed to completely ablate the area of the average arrhythmogenic site. As such, a major problem of RF ablation techniques is forming a lesion of the requisite size, which completely ablates the area of interest but does not unnecessarily destroy surrounding healthy tissue. There has been a need for ablation devices which allow for improved monitoring of the creation of a lesion, to generate linear lesions of a requisite length. The present invention satisfies this need.

It is well known that in order to effectively produce lesions using EP devices that contact with or proximity to target tissues is key. Various devices used to improve contact with sites of interest in the heart other than the isthmus region are known in the art. Basket-shaped or volume filling devices like basket-shaped catheters which expand to contact opposing heart wall sections, such as that disclosed in U.S. Pat. Nos. 5,228,442 and 5,908,446 to Imran and U.S. Pat. No. 5,465,717 to Imran et al., are known. Another device to provide efficient contact between the treatment device and a site of interest is disclosed in U.S. Pat. No. 5,482,037 to Borghi where a catheter having an electrode on a flexible member which is shaped by a control wire forms a manipulable unit adapted to achieve configurations advantageous for providing a section capable of improved contact of the electrode with tissue. U.S. Pat. No. 5,879,295 to Li et al. discloses a device having multiple electrodes that may be manipulated in a similar manner, except that the two control wires are connected apart from each other near the distal end of the device. Such a configuration allows for the formation of more complex shapes in using the device. Further, U.S. Pat. No. 5,895,417 to Pomeranz et al. discloses a catheter having a resilient, looped end with a section with electrodes. Either end of the loop may be advanced or drawn back to provide various shapes in order that the effective section of the catheter may better conform to a region. The non-active section of the loop may be used to bias the loop against a wall opposite the ablating electrodes portion to press the electrodes into improved contact with the wall it abuts.

Also, steerable or deflectable tip catheters and catheters with preformed curved sections that may be straightened for delivery purposes have been used to provide an electrode interface region conformable with particular regions in the heart. EP devices having simple J or C-shaped curved sections are known. U.S. Pat. No. 5,170,787 to Lindegren discloses a catheter utilizing a J-shaped preformed wire wherein the device has an ablating electrode at the tip. Also, there are EP devices where the curved shape is extended. U.S. Pat. Nos. 5,673,695 and 5,860,920 to McGee et al. disclose a device with a generally-circular or pigtail electrode array that may conform to the circumferential geometry of a selected annulus region in the heart. Both preformed and deflectable means of achieving the desired shape are disclosed therein. U.S. Pat. No. 5,462,545 to Wang et al. discloses a device having electrodes where the device may be formed in a planar spiral and a corkscrew configuration in addition to a generally circular shape. Further, U.S. Pat. No. 5,823,955 to Kuck et al. discloses an EP device with a distal end portion curving in one direction and switching back in an opposite direction. In all, such shapes are provided to enable improved accessibility to and/or interface with a treatment site in the heart.

The present invention also addresses the need for improved accessibility to and/or interface with the heart wall. However, the present invention meets the challenges presented in the treatment of arrhythmia by forming lesions between the tricuspid annulus and the inferior vena cava, i.e., in the "isthmus" region of the heart. Such lesions may be highly effective in treating atrial flutter by breaking abnormal circuits. While the isthmus has become an area of increasing interest, treating the region is complicated by the irregularity of the anatomical geometry and variation of the region from one patient to another. Ridges, crevasses, bumps and the like make uniform contact with the atrial wall for ablation and/or mapping in this region difficult. None of the devices noted above can perform effectively in RF ablation of the isthmus region.

The present invention provides a device and methods specifically adapted to face the challenges in ablating the isthmus region. An EP device utilizing variations on a shape having particular functional advantages is provided. The advantageous shape of the device allows it to be manipulated in a new manner which forms part of the invention.

SUMMARY OF THE INVENTION

This invention is directed to a electrophysiology (EP) device suitable for mapping functions and/or forming ablations or lesions in the isthmus region of a human patient's heart. The EP device of the invention has electrodes along the outer surface of the device and may have temperature sensors to work in concert with the electrodes. When prepared for use the catheter-like device assumes a shape specialized to advantageously interface with the isthmus region to form lesions. Lesions formed may be made in the form of linear ablations particularly suitable for eliminating or minimizing atrial flutter and/or fibrillation by isolating sections of the patient's atrial wall.

The EP device of the invention generally comprises an elongated shaft having a lumen and a proximal section, a distal section, and a plurality of at least partially exposed electrodes disposed on an outer surface of the distal section. A pre-formed forming member is provided in the lumen to shape the distal section of the device transition. Generally, the distal section is shaped in the form of a modified or flattened pigtail configuration with at least a terminal anchor region, and an intermediate interface region. A plurality of electrodes are spaced along a length of the interface section. Also, a tip may be provided at the end of the anchor region. The tip may be any typical atraumatic tip or a smooth, rounded member preferably comprising a radiopaque material. As with the electrodes, the tip may be connected to an electrical energy source to form an active or "hot" member to serve as an ablating electrode.

The electrodes on the distal shaft section form a lesion from within a patient's heart chamber when electrical energy, preferably RF energy, is emitted therefrom. The electrodes may be combination sensing and ablation electrodes which are capable of ablation and detection of electrical activity from within the patient's body. In a preferred embodiment, the electrodes on the device (including the tip, if desired) are independent, for monopolar mode use with an electrode in contact with the exterior of the patient's body for ablation. Alternatively, the electrodes may be configured in a bipolar mode for use as pairs of sensing electrodes on the shaft. A presently preferred electrode is in the form of a helical coil for improved device flexibility, although other designs are suitable including cylindrical bands, arcuate bands, strands, ribbons or the like. For high resolution sensing, the electrodes on the interface section or region may be spaced in a compact array. For sensing or ablating regions other than those opposing the interface region, additional electrodes, possibly closely packed, may be provided on the catheter as well.

A presently preferred embodiment of the invention includes at least one temperature sensor provided to monitor lesion formation placed between adjacent electrodes. To form an effective lesion in the tissue of the heart, the tissue generally should reach a temperature between about 50° C. to 70° C. Above this temperature, extensive tissue damage beyond the desired treatment site may occur as steam forms and ruptures tissue. However, to effectively ablate an arrhythmogenic site, individual lesions formed by adjacent electrodes must come together to form one continuous lesion that completely ablates an area of interest. If there are gaps in-between the lesions, they may not terminate the arrhythmia. By monitoring the tissue temperature, the physician is able to ensure that adequate heating is achieved so adjacent lesions meet or overlap to form as continuous a lesion as possible in view of the anatomical/geometric challenges presented. Such monitoring also allows a physician to avoid over-heating tissue which could cause the charring of the tissue and coagulation of surrounding blood.

To further avoid excessive temperatures, the device of the invention may also include fluid directing passageways which extend radially or longitudinally to facilitate delivery of cooling fluid. The temperature sensors may be thermocouples, although other suitable temperature sensors may be used, such as thermistors or other temperature sensing means.

The shaft of the distal section of the EP device is formed at least in part of individually-insulated electrical conductors that are electrically connected to individual electrodes on the distal section. Preferably the electrical conductors are braided. Individual wires in the distal shaft section are typically connected to temperature sensors, and, in the case of thermocouple temperature sensors, have a distal end which forms the temperature sensor. The temperature conductor wires may be braided with the electrical conductor wires. A plurality of polymer strands formed of nylon, DACRON® or the like may also be braided either with the wires or braided separately and incorporated into the sheath. Where an electrically hot tip is to be used in the catheter, the forming wire itself may be the electrical conductor. The proximal ends of the conductor wires are typically connected to individual pins of a multi-pin connector for energy and data delivery to whatever control unit and/or energy source the EP device is coupled.

The shaped end of the catheter will typically be straightened by a delivery sheath at some point prior to introduction into a guiding catheter. However, the EP device of the present invention may be constructed so as to be remotely manipulable into its desired shape using such structure as known to those with skill in the art, as for typical deflectable catheters. Also, the device may use a shape-memory alloy that assumes the desired shape when a preset temperature of the metal is reached. Naturally, such a device could be activated by heat of the body or by the application of electrical energy causing resistive heating of the material. To remove the device, especially where a preformed core member is utilized, the delivery or guide sheath may be used to once again straighten the device.

Depending upon its construction, the EP device of the invention may be used alone or with a variety of shaped or shapeable guide members. In one presently preferred embodiment, the EP device is used with a deflectable guiding catheter having a lumen which slidably receives the EP device of the invention and a distal section that can be deflected in either of two directions away from the guiding catheter longitudinal axis, such as a NAVIPORT® unit as described in copending application Ser. No. 09/001,249, filed Dec. 30, 1997, titled Deflectable Guiding Catheter to Qin, et al.

Once delivered through the inferior vena cava into the right atrium, the EP catheter is used by manipulating the device so as to hook the end of the device within the tricuspid valve of the heart. The end which passes into this region, whether it seats between cusps or not, serves as an anchoring portion when the surgeon partially retracts the catheter. This retraction puts tensile stress on the form of the EP device causing it to straighten somewhat. As it straightens, the interface portion of the catheter having electrodes is biased against at least a portion of the myocardial tissue of the isthmus. When in such close proximity, ablation may effectively occur. Preferably, this is performed by selecting only those electrodes in contact with the target tissue and applying RF energy to each (independently or in combination) and monitoring the temperature of tissue elevated by the heat generated as a result of the RF energy until a desired temperature is reached. Such steps may be carried out progressively by retracting or advancing the anchor region of the catheter to alter which tissue the interface region is biased against upon retraction. Further, upon complete retraction of the anchor region from the tricuspid valve, the hot tip may be placed into contact with tissue in difficult to reach recesses where upon RF energy is applied to ablate the tissue site and form a full, linear lesion made.

The catheter of the invention is configured for effective EP treatment of the isthmus region of a mammalian heart. This is to be achieved by a combination of the advantages provided by features of the catheter including, but not limited to, the shape of the catheter and placement of electrodes of the temperature sensors for monitoring of the lesion formation, and the RF active ablating tip disclosed. Ablation of the isthmus of a heart to treat atrial flutter and/or atrial fibrillation is further to be achieved by the method of manipulating the catheter as described herein.

DETAILED DESCRIPTION OF THE INVENTION

Before explaining the invention in detail, it is to be understood that the invention is not limited to the embodiment described or as shown in the figures and that elements of the EP device may be variously included or disincluded without departing from the invention. In point of fact, any conventional construction may be employed which is suitable for producing an ablation or micro-ablation device, which may be set in the shape disclosed that is critical to the functionality of the invention in treating the isthmus region of the heart.

Figure 1:
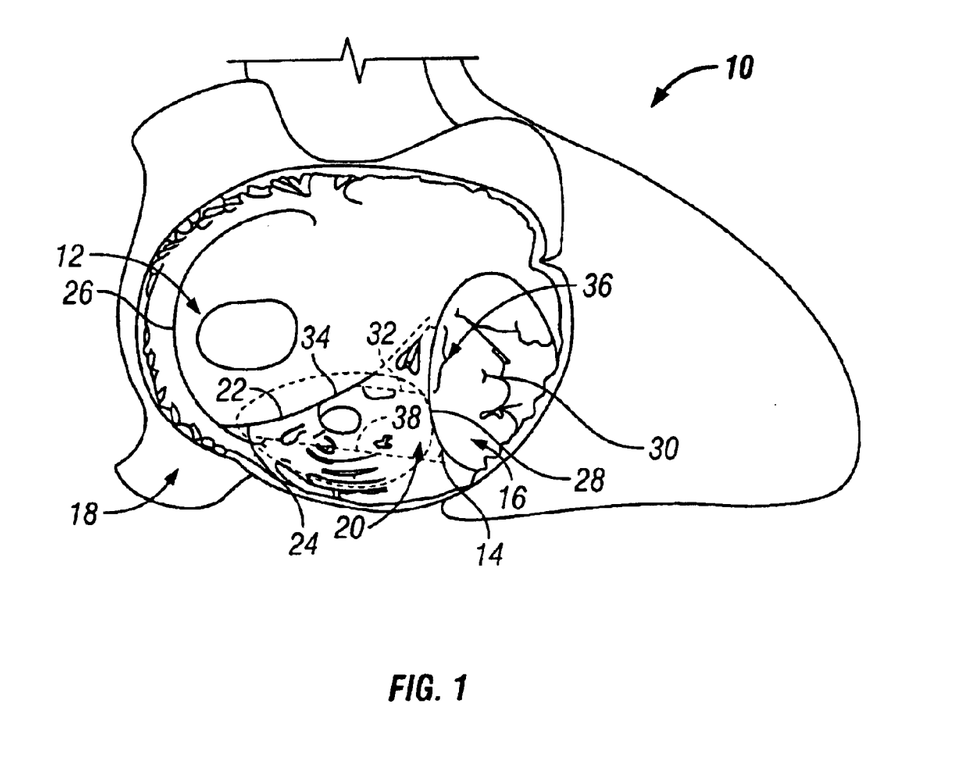
FIG. 1 is a diagrammatic view of portions of a human heart showing the isthmus region.

FIG. 1 diagrammatically illustrates the target region for treatment by the EP device of the invention. The heart 10 is shown in isolation with right atrium 12 open. Generally, the isthmus region is the area 14 bounded by the tricuspid valve 16 anteromedially and the inferior vena cava 18 posterolaterally. At least a significant portion of this region is more formally referred to as the "posterior isthmus" or "inferior vena cava-tricuspid isthmus." A section of the isthmus 14 known as "septal isthmus" 20 is generally considered to be the posterior-inferior part of the right atrium 12. Further, a portion of the isthmus 14 known as the "isthmus quadrilateral" has been defined. This is the section of the right atrial wall that is identified as the region bounded by the extension line 22 of the eustachian valve 24 and ridge from the terminal crest 26, the hinge line 28 of the septal leaflet 30 of the tricuspid valve 16, a line 32 traced between the superior extent 34 of the ridge of the eustachian valve 24 and the tricuspid valve 16 orifice at the base of the triangle of Koch 36, and finally by a line 38, spanning the termini of lines 22 and 28.

One study of this region, titled "The Architecture of the Atrial Musculature Between the Orifice of the Inferior Caval Vein and the Tricuspid Valve: The Anatomy of the Isthmus" by J. Cabrera et al., observed the following measurements (in mm) among a sample of healthy human heart specimens:

| Line No. | Mean +/− Standard Deviation | Range |
| --- | --- | --- |
| 22 | 31 +/− −5 | 22–47 |
| 28 | 33 +/− −5 | 20–43 |
| 32 | 26 +/− −4 | 16–32 |
| 38 | 31 +/− −4 | 19–40 |

In addition to the large variances in the size of the isthmus quadrilateral, marked differences in the atrial wall forming the region were noted. Such differences in the texture in the form of ridges or tribiculation further complicate treating the isthmus.

Figure 2:
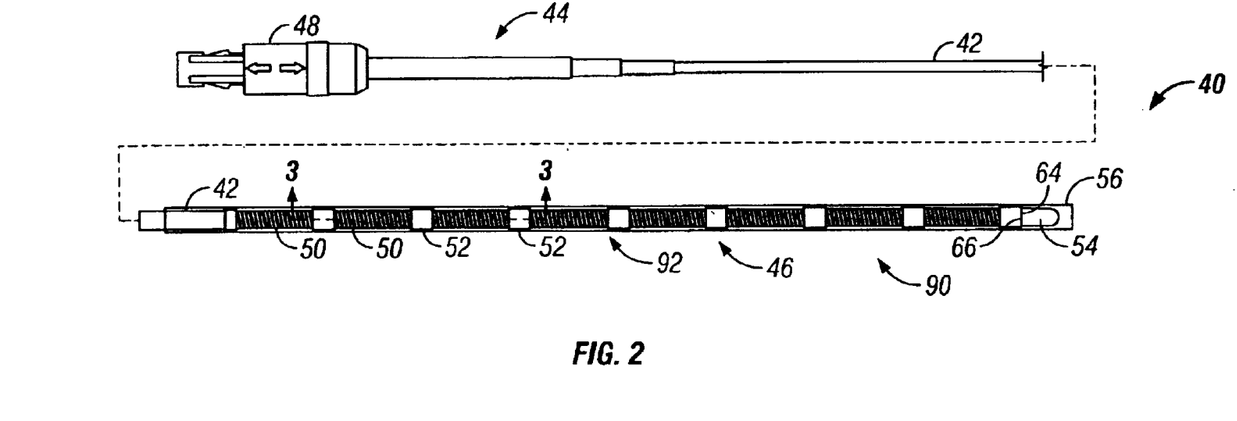
FIG. 2 is a diagrammatic view of the EP device of the invention in its constrained configuration.

As previously stated, the EP device of the invention and the manner of employing it are provided to enable effective treatment of the isthmus region despite its variation in structure both within a heart and among patients. As shown in FIG. 2, the EP device 40 of the invention generally comprises an elongated shaft 42 having a proximal section 44 a distal section 46, an electrical connector 48 on the proximal end of the device 44, a plurality of electrodes 50 on the distal shaft section 46, a plurality of temperature sensor members 52 on the distal shaft section 46 with at least one temperature sensor between the electrodes 50, and a smooth, rounded tip 54 at the distal end of the device. A presently preferred material for the tip 54 is a radiopaque metallic material such as platinum, gold, stainless steel and alloys of each. The EP device 40 illustrated in FIG. 2 is shown in a straightened configuration constrained by guide member 56. Upon removal of member 56, the device 40 assumes its working shape.

Figure 3:
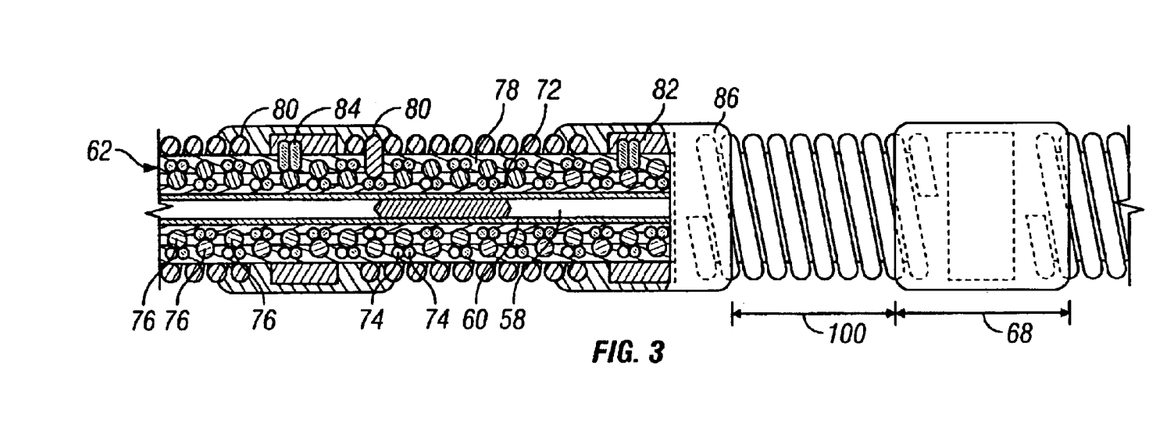
FIG. 3 is a partial cross-sectional view of the same EP device shown in FIG. 2 taken along the lines 3—3.

In FIG. 3, an embodiment of the EP device 40 in the form of a catheter with a core member or forming member 58 set within a lumen 60 extending within the catheter body, shaft or sheath 62 is shown. The forming member 58 is connected to the tip 54 by suitable method such as insertion within a recess in the tip 54 and using silver alloy braising paste to secure each. The connection may be conducting so that the tip 54 serves as an electrically "hot" member with member 58 functioning as an electrical lead.

Figure 6:
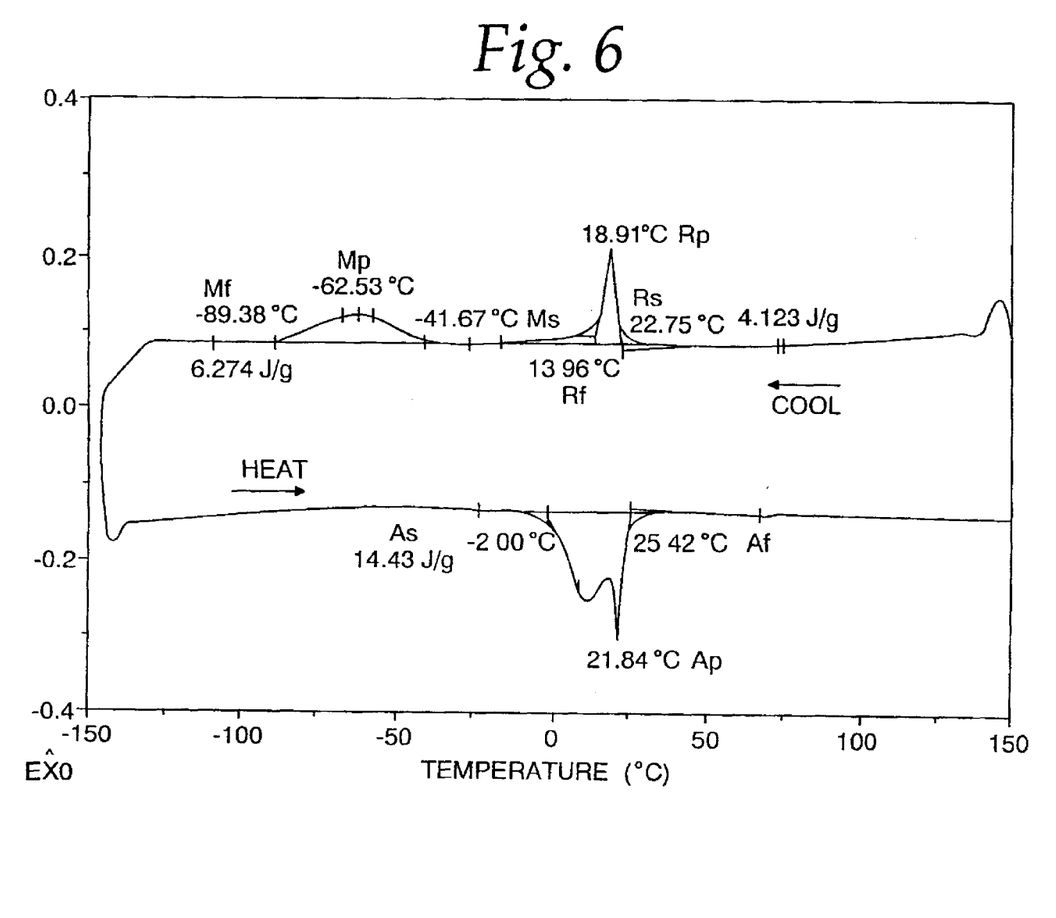
FIG. 6 is a diagram for material of an ememplary form of a forming member of an embodiment of the EP device shown in FIG. 2.

The forming member 58 is preferably a NITINOL (or other Ni—Ti alloy) wire at a maximum diameter of about 0.01 in (0.25 mm) to about 0.020 in (0.051 mm). The distal section 46 preferably has a nominal diameter of about 0.014 in (0.36 mm). Though not shown, the forming member 58, and preferably a distal section thereof, may be tapered and/or flattened. Where member 58 is wire, it may be shaped into an appropriate form through controlled heating while constrained in a forming fixture. An exemplar procedure is to preheat an oven to 1184° F. (640° C.) and then to heat a forming fixture loaded with NITINOL wires from room temperature to 977° F. (525° C.) in that oven. Following this, the form and wire(s) will be quenched in room temperature tap water. The exemplary wire 58 treated in this manner was DSC tested and displayed the profile depicted in FIG. 6.

Use of other types of wire for forming member 58 is contemplated in the invention such as stainless steel wire, music wire, titanium wire or superelastic or shape-memory wire other than the alloys of Ni—Ti. Use of other shaping methods within the level of skill in the art, such as cold-forming the wire, are also contemplated. Further, a composite material such as made with carbon fiber, KEVLAR®, DACRON® or fiberglass, may be used for the forming member 58.

Also it is to be understood that the forming member 58 need not be a central member disposed within a catheter body 62. Other constructions not shown where the EP device is provided an appropriate shape for its intended purpose will suffice. A differently configured forming member or multiple members may be integrated in to the catheter body 62 to provide the required shape of the EP device. Alternately, the catheter body 62 itself may be constructed of a material or in a manner where no separate forming member is needed. The lumen 60 may either remain or not.

In the illustrated EP device embodiment presently preferred, after the tip 54 is affixed to the wire 58 and the subassembly is cleaned, the forming member 58 is provided with a partial jacket 70 extending 4 in (10 cm) to 6 in (15 cm) proximally from the shoulder section 64 of the tip. The jacket 70 comprises an insulating polyester heat shrink tubing originally about 0.0035 in (0.089 mm) thick and sized to slip over the forming wire 58 prior to heating.

As illustrated in FIG. 3, for the preferred catheter body subassembly 62, a first polymeric layer 72 comprises a polyamide tube originally at 75 in (190 cm) with 0.16 in ID×0.018 in OD upon which is braided, at 24 pitch width, thermocouple wires 74 and electrical conductors 76. Over the distal 3.15 in (8 cm) of the braid, a second polymeric layer 78 comprising a thin-walled (originally 0.003 in (0.076 mm) tetrafluoroethylene hexafluoro propylene vinylidene fluoride mixture (THV) or other fluorropolymer is laminated. This structure is formed over a TEFLON® beading 86.6 in (220 cm)×0.15 in OD (3.8 mm) which is removed when the subassembly 62 is complete.

After exposing selected sections of braided wire, electrode coils 50 optionally in the form of helical coils of platinum/iridium and temperature conducting thermocouple bands 82 preferably of gold are connected to the appropriate wires with gold-tin wire solder. Interelectrode spacing 68 is preferably between about 1 mm to about 3 mm and most preferably 2 mm in order to accommodate a temperature sensor between electrodes. In a preferred embodiment, the exposed length 100 of the electrodes is between about 2 mm and about 8 mm. In a preferred embodiment of the device 40, the electrical conductors 76 are formed of 36 AWG copper wire having a polyimide insulating coating of about 0.0005 inch thick (0.013 mm) and temperature sensors 84 are T-type thermocouples formed by connecting thermocouple wires 74 comprising 41 AWG copper and constantan wires having a polyimide insulating coating of about 0.00025 in (0.007 mm) to about 0.0005 in (0.013 mm) thick. In the embodiment of the EP device illustrated in FIG. 3, the distal ends of the thermocouple wires are joined together so that the thermocouple formed therefrom measures the temperature at the interface of the two wires. Alternatively, the distal ends of the thermocouple wires may be individually secured to the conducting member 76 in a spaced-apart configuration so that the thermocouple measures the temperature along the length of the conducting member 76 between the distal ends of the thermocouple wires.

In a presently preferred embodiment as shown in FIG. 2, about 4 to about 12 coil-type electrodes 50 are provided on the distal portion 46 of the EP device. An 8 electrode coil variation is pictured. In addition, the device 40 may be adapted or configured so tip 54 may is a "hot" tip to also serve as an electrode. The thermocouple wires 74 and electrical conductor wires 76 and core wire 58 are to be in electrical communication with connector 48. Presently, a 26 pin connector (available through LEMO USA) is preferred. Where the invention is to be produced without temperature sensors, a hot tip or fewer electrodes, a connector with a lower pin count, e.g. 9 to 16 pins, may be preferred.

Referring again to FIG. 3, a third polymeric layer 86 comprising THV or other fluoropolymer having an initial 0.052 in ID (1.3 mm)×0.061 in OD (1.55 mm) may be laminated over the thermocouple conducting members 82, between electrodes 50 and the remainder of the body 62. The third polymeric layer 86 may cover at least the ends 80 of the electrodes 50 as shown to prevent exposure of a sharp metallic edge of the electrode to tissue. Alternatively, where the third polymeric layer 86 does not partially cover the electrode ends 80, any gaps between electrodes 50 and thermocouples may be filled-in with an adhesive (preferably LOCTITE 3811, available from 3M) and cured using ultraviolet light (UV). Optionally, the polymeric layer 86 may cover all but the portions of the electrodes 50 intended to interface with the isthmus region.

The polymeric jacket 86 covering conducting member 82 insulates the temperature sensors 84 from noise (e.g. RF noise) present as a result of the energy sent to the electrodes 50. In an alternative embodiment, however, the jacket may be omitted altogether, for example, where filtering capability against signal noise is provided. Similarly, the thermocouple may be attached directly to the electrode coil for a faster and more accurate response where the noise from the electrode energy is otherwise filtered. Such filtering may be accomplished by hardware known to those with skill in the art, including an appropriately programmed general purpose computer.

As shown in FIGS. 2 and 3, the preferred EP device 40 is prepared for use by inserting a proximal portion of the forming member 58 (shown in variations of its basic shape in FIGS. 4a and 4b) into the lumen 60 leaving at least the shaped portion 88 of the forming member 58 exposed. Next, a restraining guide or tube 56 is provided over the distal end of the catheter body 62. Optimally, the guide 56 has a length of about 3 in (7.6 cm) and is sufficiently stiff to fully straighten and hold straight the shaped portion of the forming member 58 which is drawn into the catheter body 62 after the wire is cooled below the $M_f$ (martinsite finish temperature) point of the Ni—Ti material selected. When the core member 58 returns to room temperature, the less-curved and consequently less-stressed portions of the wire will change into an austenetic phase. When optional tip 54 is used, after member 58 is drawn into the catheter body 62, shoulder section 64 is laminated with THV resin (preferably THV 200, available from 3M) to the edge 66 of the distal end 46 of the catheter body sheath 62.

Figure 4A:
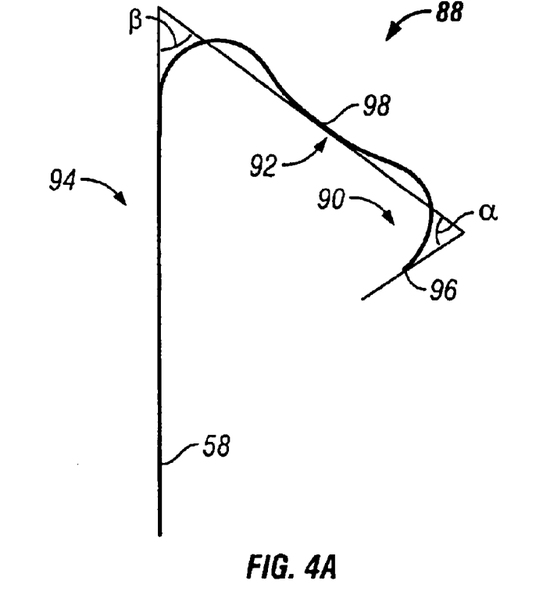
FIGS. 4a and 4b are diagrammatic views of exemplary shapes for the forming member employed in the EP device of the invention.
Figure 4B:
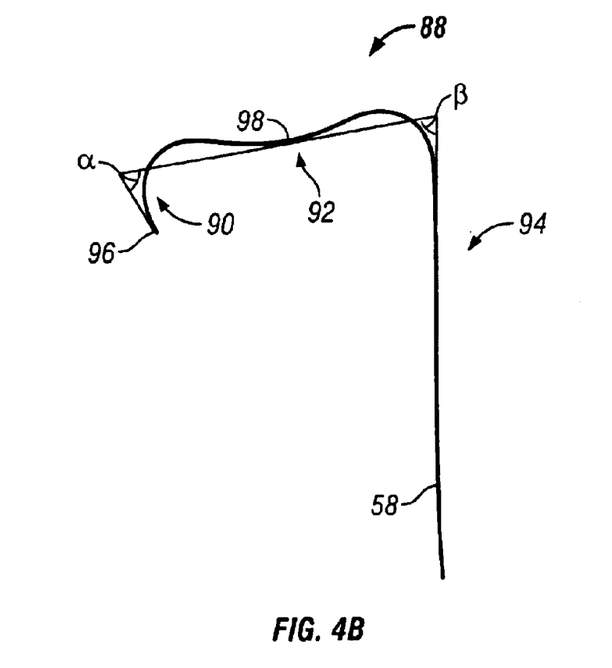
Figure 5A:
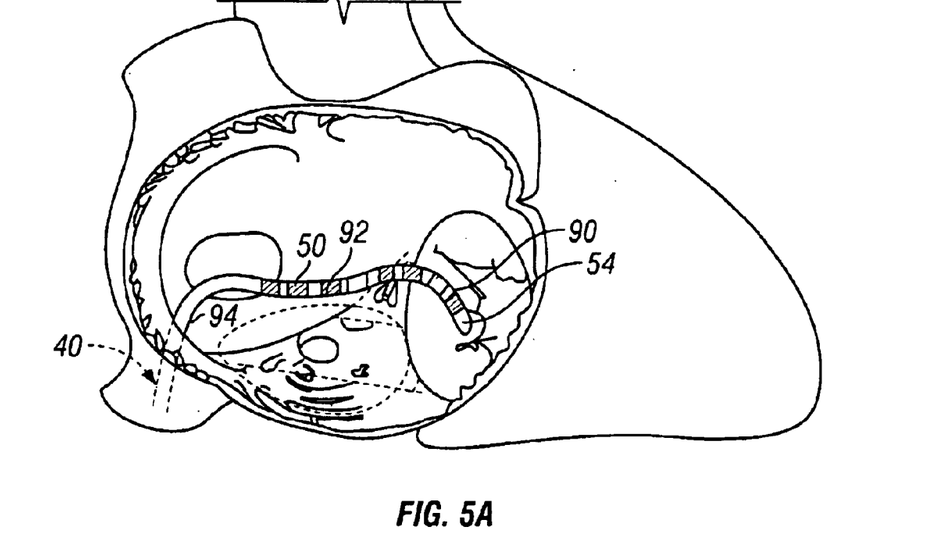
FIGS. 5a–5d are a series of diagrammatic views demonstrating the EP device of the invention when unconstrained and in various stages of use.

When the restraining guide 56 is removed from the EP device 40 (as illustrated in the FIGS. 2 and 3 in its constrained configuration), it has an unconstrained shape similar to that pictured in FIG. 5a which is substantially like that of the bare forming members 58 shown in FIGS. 4a and 4b. Such a form is assumed by the complete assembly since the catheter body 62 will preferably conform, in large part, to the shape of the forming member 58. Where a stiffer catheter body or sheath 62 is to be used, it may be advantageous to use a heavier forming member to overcome its resistance. The EP device may not, however, be so stiff that manipulation according to the invention will damage tissue, particularly the tricuspid valve 16. On the other hand, it may not be so flexible that it will be ineffective for its intended use. The construction as set forth above is within the acceptable range to enable use of the EP device.

The overall size of the shapes may be varied to account for different-sized hearts. Shapes structurally equivalent in nature are intended to be covered by the invention. However, the shape of the unconstrained EP device 40 comprises at least an "anchor" region or section 90 an "interface" region or section 92. The anchoring portion 90 of the EP device 40 and corresponding section of the forming member 58 is a section between about 0.4 in (10 mm) and about 0.6 in (15 mm), oriented substantially as shown in FIGS. 4a, 4b or 5a. The interface portion 92 of the EP device 40 and forming member 58 is a section between about 3 in (76 mm) and about 5 in (127 mm) and is likewise oriented substantially as shown relative to the shaft 94. At least a majority of the electrodes 50 are located along the interface portion 92 in the assembled EP device 40. However, either more or less may be provided according to the physiological requirements of a given patient, especially in view of the optimal length of the interface section 92. The interface section 92 is optimally in the shape of a compound curve as shown. Provision of such a curve, or other inwardly-tending or bowed/arcuate profile greatly assists in biasing the catheter body 56 against the isthmus region upon retraction of the device 40. Additionally, section 92 may include at least a portion which is straight. The first region or anchor region 90 as variously described may be curved or be at least partially straight as well. Transition regions between the various sections may be small, large or blended curves. Preferably, where simple curves are used, they will variously have radii of curvature between about 0.1 in (2.5 mm) and about 0.5 in (13 mm). Most preferably, each transition has a radius of curvature of 0.3 in (7.6 mm).

Of course, in addition to describing the portions of the EP device in functional terms, it is also possible to express them as first, second and third sections or the like corresponding to the portions 90, 92 and 94, respectively. The geometric relation of these sections to one another may be considered in vector notation, radial coordinates or otherwise. An angle α defined by a tangent to the end 96 of the first section 90 and a central portion 98 of the second section 92 may be between about 60° and about 90°. More preferably between 60° and 70°; most preferably at 70°. An angle β defined by tangents to a central, most convex portion 98 of the second section 92 and the third section 94 may be between about 30° and about 90°; most preferably about 90°. It is specifically stated that any specific angle, range of angles, or combination of angles or ranges of angles and/or of lengths disclosed with the exemplar instances provided is expressly considered to be part of the invention.

As noted above, the shape of the EP device 40, imparted in the preferred embodiment by forming member 58, enables the way it may function in the setting of the human heart to treat a site at or near the isthmus region 14. Such function is illustrated in FIGS. 5a–5d.

Figure 5B:
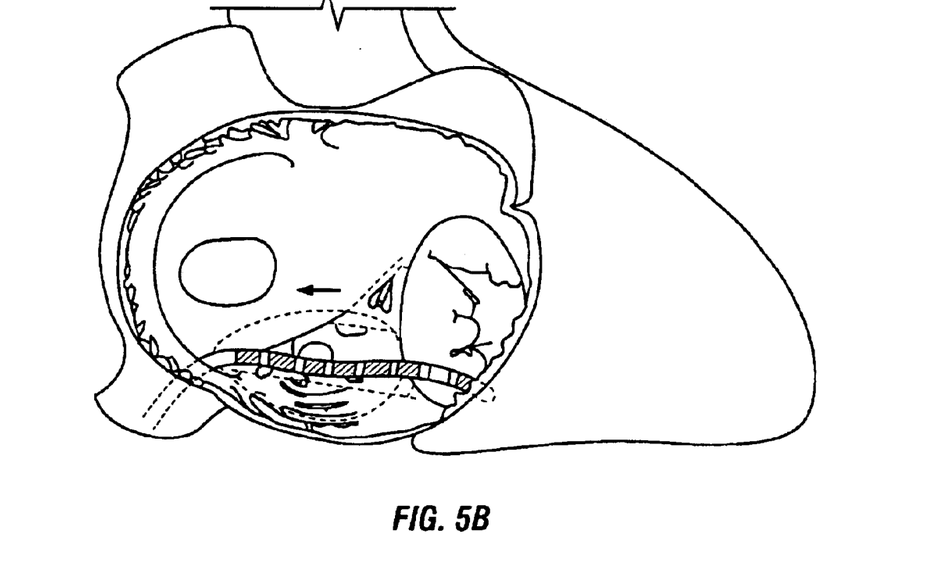

As shown in FIG. 5a, upon introduction into the right atrium, section 90 of the device is hooked in the region of the tricuspid valve 16 by advancement in the direction of the arrow. It may be placed between leaflets or on leaflets of the valve 16. As shown in FIG. 5b, upon retraction of the EP device 40, section 92 is forced into contact with the isthmus region 14. Retraction of the device as shown provides contact pressure with the atrial wall in the desired area of the isthmus to form a lesion. Depending on the construction of the EP device 40 and tensile force applied in retraction, the atrial wall at the isthmus may actually be deformed slightly to place the electrodes 50 in contact with heart tissue otherwise at the bottom of a crevasse or the like. Increased bowing of the interface section 90, will facilitate the application of greater pressure by the catheter body 56 in the isthmus region 14 to achieve such ends.

Upon achieving the intended contact, it may be desired to use the electrodes to first sense electrical activity or "map" the site with which contact has been achieved. When sensing electrical activity essentially all of the electrodes 50 can be simultaneously employed. Whether after mapping or simply after achieving the contact as diagrammatically pictured in FIG. 5b, electrical energy (preferably RF energy) is transmitted to the electrodes 50 to ablate the tissue. When performing the ablation, the typical procedure is to direct the RF current to one or two electrodes at the most distal end of the EP device to perform the first ablation and then continue proximally one or two electrodes at a time until an ablation of desired length is obtained in the atrial chamber. This will reduce the overall power requirements for the EP device 40. The temperature sensors (if included in the EP device) detect the temperature of the heart wall between the adjacent electrodes, so that the electrical power delivered to each electrode can be controlled by a suitable device (such as an RF generator or other device) to control the temperature in a desired manner, and to gauge when a continuous lesion has been formed and, therefore, when to move proximally to the next electrodes. However, simultaneous delivery of RF energy to either a select number or all electrodes is possible (with or without the use of a multiple channel temperature sensing device) where a sufficient power source is provided. Feedback of the temperature data can be used to modulate the power and prevent thrombus formation in the preferred use. Cooling fluid (possibly delivered through a lumen in the device) may be used, either independently or in combination with temperature feedback control as described in copending application, Ser. No. 08/629,057, titled Linear Ablation Device and Assembly to Schaer.

Depending on the success in forming a complete lesion, as may be indicated by temperature sensors on the EP device, or as by using the electrodes to sense electrical activity with the electrodes 50 after an ablation, the EP device may be reset and biased at another location in the isthmus region following substantially the same steps as above. Where a complete ablation in a region has been formed by virtue of the successful manipulation of the specially-adapted shape of the EP device, or where a successful lesion formed is to be lengthened or where it is simply desired to form a lesion at a different site, the steps of resetting the anchor region of the EP device in the vicinity of the tricuspid valve and retracting to bias the shape against the heart wall are simply repeated.

Figure 5C:
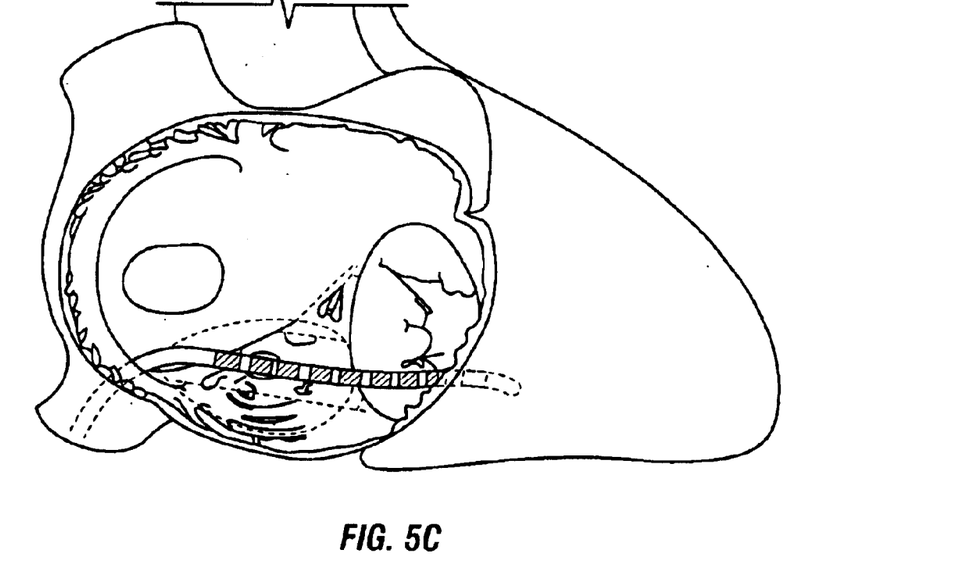
Figure 5D:
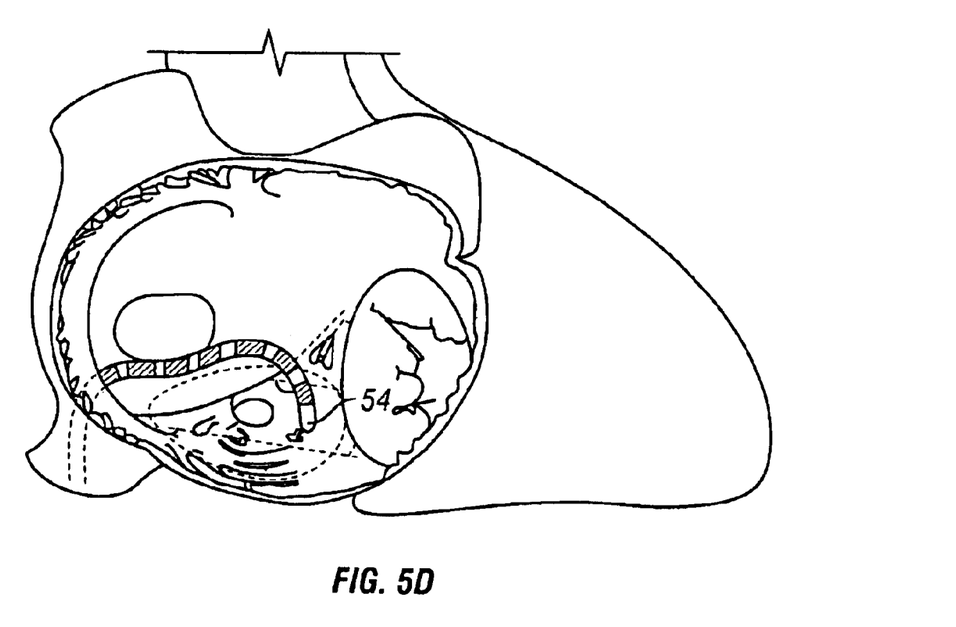

Further, use of the EP device that does not involve the hooking and retraction steps discussed above is possible. As shown in FIG. 5c, section 92 may simply be advanced so that the electrodes 50 contact an area near the septal isthmus 20 for ablation. Used in this manner, section 90 may even be placed in the tricuspid valve. Further, as shown in FIG. 5d, the device may be retracted so that region 90 is clear of the tricuspid valve 16 altogether so the tip 54 points into the atrial wall in the isthmus region 14. When the EP device is retracted so the electrically "hot" tip 16 is effectively dragged into or is otherwise placed at a site, as shown in FIG. 5d, electrical RF current may follow in order to ablate the tissue around the tip 16. Because of the shape of the EP device, it may be manipulated so the tip 54 will be forced into site of interest to achieve acceptable contact for ablation.

Each of these uses of the EP device may be employed to start a lesion, to complete one or to fully ablate a particular site requiring treatment.

In addition to where the device of the invention is an integrated unit as shown in the figures with the catheter body 62 and forming member 58 attached to one another, the device and methods described are also contemplated where the device is of a deflectable construction or where the device is in the form of a shaping member like the forming wire used in conjunction with an over-the-wire EP catheter somewhat like that disclosed in U.S. Pat. No. 5,895,355 titled Over-the-Wire EP Catheter to Schaer. The additional steps of manipulating the catheter to form one or more variations of the shape of the EP catheter disclosed herein for a deflectable catheter or inserting the forming wire once the device is otherwise prepared for use with an over-the-wire catheter are expressly considered to be part of the invention.

While the invention has been described herein in terms of certain preferred embodiments, methods of use and preparation for use, a variety of modifications and improvements may be made to the present invention without departing from the scope thereof. Also, those features of the invention discussed above, as related to the figures, are merely preferred and consequently may be varied without departing from the scope of the invention. Furthermore, it is to be understood that the manipulated shapes formed by the EP device in carrying out the treatment method or methods described herein also form part of the invention. Finally, all U.S. patents and applications, to which reference has been made, especially in describing possible variations in the present invention are incorporated by reference in their entirety herein.

What is claimed is:

1. An electrophysiology device for ablating the isthmus region of the heart adjacent to the tricuspid valve, the device comprising:

an elongate shaft having a predetermined operable configuration including a proximal portion extending in an axial direction and an operable distal portion extending transverse to the axial direction;

a hook end region of the shaft distal portion generally extending toward or along the axial direction of the proximal portion of the elongate shaft in spaced relation thereto for anchoring to the tricuspid valve of the heart;

an interface region of the shaft distal portion extending between the proximal portion and the hook end region; and a reverse curved portion of the interface region that bows the distal portion back inwardly for providing intimate contact with the isthmus region with retraction of the shaft distal portion and engagement of the hook end region with the tricuspid valve for an ablation operation on the isthmus region wherein the operable distal portion includes an arcuate region between the proximal region and the interface region with both the arcuate region and hook end region bowing outwardly opposite to the inward bowing of the interface region.

2. The device of claim 1 wherein the shaft comprises a forming member of flexible, shape retentive material having a preformed configuration substantially matching that of the predetermined operable configuration of the shaft, and a sheath for receiving the forming member in an insertion configuration for delivery to the isthmus region restrained against returning to the preformed configuration thereof.

3. The device of claim 1 wherein the operable distal portion including the hook end and interface regions define a compound curve.

4. The device of claim 1 wherein the operable distal portion includes an arcuate region between the proximal portion and the interface region with both the arcuate region and hook end region bowing outwardly opposite to the inward bowing of the interface region.

5. The device of claim 1 wherein the interface region includes an innermost portion thereof due to the inward bowing thereof and the hook region has a free end and an arcuate configuration bowing outwardly so that the free end is an innermost portion thereof.

6. The device of claim 1 wherein the hook region has a distal end portion, and the reverse curved portion and distal end portions define respective tangent lines therewith such that the reverse curved portion tangent and the proximal portion of the shaft form an approximate angle of between 30 and 90 degrees, and the tangent lines form an approximate angle of between 60 and 90 degrees.

7. The device of claim 1 wherein the hook region has a curved configuration generally opposite to that of the reverse curved portion with the curved hook region generally opening toward the shaft proximal portion.

8. The device of claim 1 wherein reverse curved portion is bowed inwardly in a direction generally toward or along the shaft proximal portion for biasing the reverse curved portion into engagement with the isthmus region of the heart.

* * * * *

UNITED STATES PATENT AND TRADEMARK OFFICE
CERTIFICATE OF CORRECTION

PATENT NO. : 6,746,446 B1
DATED : June 8, 2004
INVENTOR(S) : E. Richard Hill, III et al.

It is certified that error appears in the above-identified patent and that said Letters Patent is hereby corrected as shown below:

Title page,
Item [75], Inventors, change "Mahmoud R. Seraj, Mountain View, CA" to
-- Mahmoud K. Seraj, Apex, NC --.

Signed and Sealed this

Eighteenth Day of January, 2005

JON W. DUDAS
*Director of the United States Patent and Trademark Office*